(12) United States Patent
Noda

(10) Patent No.: US 6,878,156 B1
(45) Date of Patent: Apr. 12, 2005

(54) PORTABLE COOLER FOR HEAT EXCHANGE CATHETER

(75) Inventor: Wayne Arthur Noda, Mission Viejo, CA (US)

(73) Assignee: Alsius Corporation, Irvine, CA (US)

(*) Notice: Subject to any disclaimer, the term of this patent is extended or adjusted under 35 U.S.C. 154(b) by 0 days.

(21) Appl. No.: 10/207,410

(22) Filed: Jul. 26, 2002

(51) Int. Cl.[7] .................................................. A61F 7/00
(52) U.S. Cl. .......................................... 607/106; 607/104
(58) Field of Search ................................ 607/106, 104, 607/105, 96, 101, 102, 113, 116; 606/28; 604/113, 49, 114

(56) References Cited

U.S. PATENT DOCUMENTS 5,125,069 A * 6/1992 O'Boyle ...................... 392/465
6,673,098 B1 * 1/2004 Machold et al. .............. 607/96

* cited by examiner

*Primary Examiner*—Henry Bennett
(74) *Attorney, Agent, or Firm*—John L. Rogitz

(57) ABSTRACT

A portable cooler is provided for heat exchange catheters that is powered by one or more batteries. The cooler can include Rankine cycle compressor components or thermoelectric cooler (TEC) components. The cooler can be carried in an ambulance and used to support coolant to an indwelling heat exchange catheter that is placed in the patient's venous system to prevent fever and/or induce therapeutic moderate hypothermia in, e.g., stroke victims, heart attack victims, and cardiac arrest victims.

18 Claims, 2 Drawing Sheets

PORTABLE COOLER FOR HEAT EXCHANGE CATHETER

FIELD OF THE INVENTION

The present invention relates generally to coolers for heat exchange catheters.

BACKGROUND OF THE INVENTION

The present assignee has introduced heat exchangers that cool (and in some cases heat) saline that is sent in a closed loop through an indwelling heat exchange catheter for the purpose of maintaining patient temperature. The catheter can be used to prevent fever following ischemic insult or trauma or to induce therapeutic hypothermia for conditions such as stroke, heart attack (myocardial infarction), and cardiac arrest, as well as cooling for aneurysm surgery and warming after cardiac bypass operations, and other heating/cooling applications.

Of relevance to the present invention is the discovery that the medical outcome for a patient suffering from severe brain trauma or from ischemia caused by stroke, cardiac arrest, or heart attack is improved if the patient is cooled below normal body temperature (38° C.). As understood by the present invention, the medical outcome for many such patients might be significantly improved if the patients were to be moderately cooled to 32° C.–34° C. relatively quickly after an ischemic insult for a short period, e.g., 12–72 hours. It is believed that such cooling improves patient outcomes by improving the mortality rate, in that many organs can benefit from the cooling, and by improving the neurological outcome for those patients that survive.

As recognized in co-pending U.S. patent application Ser. No. 09/133,813, filed Aug. 13, 1998, owned by the present assignee and incorporated herein by reference, the above-mentioned advantages in treating ischemia by cooling can be realized by cooling the patient's entire body, i.e., by inducing systemic hypothermia. The advantage of systemic hypothermia is that, as recognized by the present assignee, to induce systemic hypothermia a cooling catheter or other cooling device need not be advanced into the blood supply of the brain, but rather can be easily and quickly placed into the relatively large vena cava of the central venous system. Moreover, since many patients already are intubated with central venous catheters for other clinically approved purposes anyway, providing a central venous catheter that can also cool the blood requires no additional surgical procedures for those patients. A cooling central venous catheter is disclosed in the present assignee's co-pending U.S. patent application Ser. Nos. 09/253,109, filed Feb. 19, 1999 and 09/305,613, filed May 5, 1999, both of which are incorporated herein by reference.

As mentioned above, it is believed that the sooner a patient is cooled after ischemic insult, the better the therapy. The present invention recognizes that many patients will have their first encounter with health care personnel in ambulances. Thus, it would be advantageous, as understood herein, to provide a means to cool these patients in the ambulance, with cooling continuing in the hospital. Heretofore, however, the heat exchangers that have been induced were not generally portable and in any case typically require AC power, both of which characteristics prevent their use in ambulances. With these recognitions in mind, the invention herein is provided.

SUMMARY OF THE INVENTION

A system for controlling patient temperature includes a portable housing and a heat exchanger in the housing and powered by at least one battery. A heat exchange element is in thermal contact with the heat exchanger, and the heat exchange element carries coolant. Also, a closed loop heat exchange catheter receives coolant from and sends coolant to the heat exchange element. The catheter is configured for placement in the circulatory system of a patient to exchange heat with the blood of the patient. The preferred heat exchanger may be based on compressor principles or on thermoelectric cooling principles.

In a preferred non-limiting embodiment, the catheter is configured for percutaneous advancement into the central venous system of the patient. The coolant preferably is not infused into the bloodstream of the patient.

If desired, a pump may be supported on the housing to pump coolant through the system. In further preferred non-limiting embodiments, tubing connects the catheter to the heat exchange element through a connector, and a quick disconnect assembly is engaged with the housing and is also engaged with at least a portion of the tubing connected to the catheter to disconnect the catheter from the housing when the housing moves past a limit of the disconnect assembly. The disconnect assembly may include a tether.

With respect to the heat exchange element, it may form an interior through which coolant flows and an exterior in thermal contact with the heat exchanger. Coolant flows through the heat exchange element through tortuous paths. The tortuous paths may be established at least in part by spheres disposed in the interior of the heat exchange element.

In another aspect, a method for cooling a patient while the patient is located in a vehicle includes disposing a dc-powered heat exchanger in the vehicle, and advancing a heat exchange catheter into the venous system of the patient. The system also includes establishing fluid communication between the catheter and heat exchanger. The heat exchanger is operated to circulate coolant through the catheter to cool the patient.

In yet another aspect, a heat exchange system that is configured for engaging, in fluid communication, an indwelling heat exchange catheter, includes a portable housing, a heat exchanger in the housing, and at least one battery electrically connected to the heat exchanger to power the heat exchanger.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
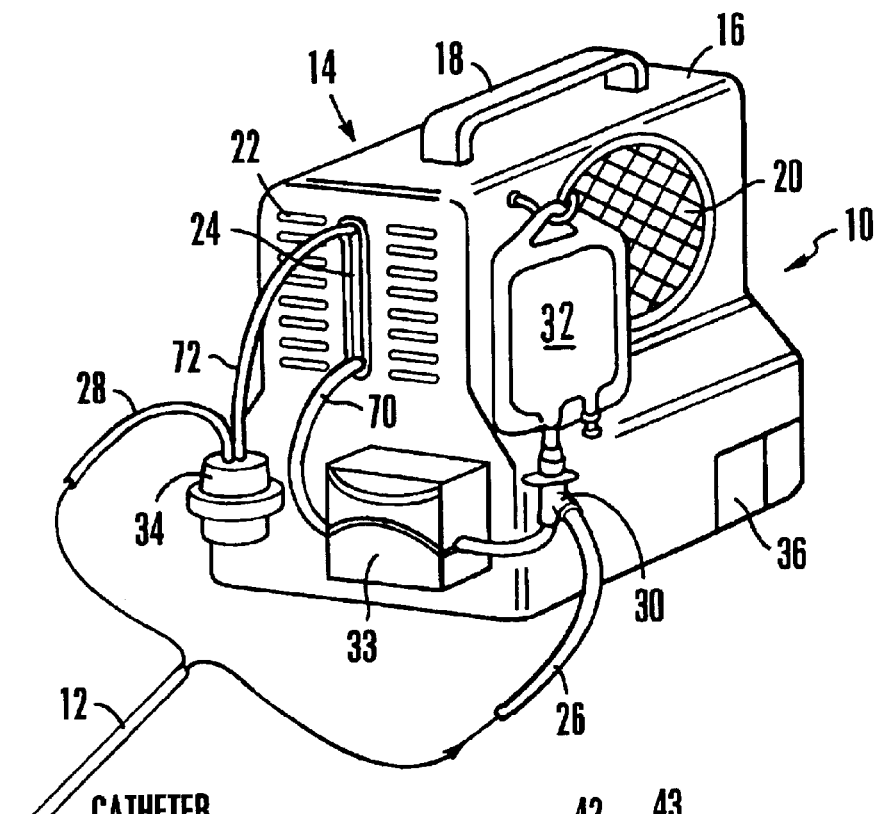
FIG. 1 is a perspective view of the present portable cooler, showing the heat exchange catheter schematically.

Referring initially to FIG. 1, a system is shown, generally designated 10, that includes a heat exchange catheter 12 that is in fluid communication with a cooler 14. While the term "cooler" is used herein, it is to be understood that the cooler 14 can in some embodiments warm coolant as well as cool it.

In accordance with present principles, the system 10 can be used to induce therapeutic hypothermia in a patient using a catheter in which coolant circulates in a closed loop, such that no coolant enters the body. While certain preferred catheters are disclosed below, it is to be understood that other catheters can be used in accordance with present principles, including, without limitation, any of the catheters disclosed in the following U.S. patents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,245,626, 6,261,312, 6,312,452, 6,325,818, 6,409,747, 6,368,304, 6,338,727, 6,299,599, 6,287,326, 6,126,684.

As shown in FIG. 1, the cooler 14 includes a lightweight portable plastic or metal housing 16 that can include a handle 18. One or more air intakes 20 can be provided on the housing 16, as well as a series of air exhaust vents 22.

A heat exchange element, described more fully below, can be received in a slot 24 of the housing 16. As shown, an inlet tubing set 26 and an outlet tubing set 28 are connected to the heat exchange element in the slot 24, and these tubes 26, 28 are connected to the catheter 12. Thus, coolant such as but not limited to saline can circulate in a closed loop through the catheter 12 and heat exchange element without exiting the loop into, e.g., the patient's bloodstream, with the coolant being cooled as it passes through the heat exchange element. The coolant in turn cools the blood.

If desired, a temperature probe can be engaged with the patient to provide feedback to the system 10 to establish a predetermined temperature, but in the preferred embodiment that is not necessary. Specifically, the preferred embodiment seeks simply to start the cooling process as quickly as possible during the relatively short period that the patient is enroute to a hospital, with longer-term controlled cooling being undertaken at the hospital. Because many hours may be required to reach target temperature in the hypothermic range, the system 10 need only commence removing heat from the patient as quickly as possible, without requiring patient temperature feedback or sophisticated control algorithms that can be employed in hospital systems.

In one non-limiting embodiment the inlet tubing set 26 can include a dual lumen IV spike 30 that interconnects an IV bag 32 of coolant, e.g., saline, with the coolant circuit established in part by the inlet tubing set 26. Also, in a non-limiting embodiment the inlet tubing set 26 can include a quick connect tubing pump 33 such as a peristaltic pump or diaphragm pump that can receive IV tubing and engage the tubing externally to pump fluid therethrough. Moreover, if desired the outlet tubing set 28 can include an air trap 34 to remove air from the saline entering the catheter 12 from the cooler 14.

As shown in FIG. 1, the housing 16 can contain or otherwise support one or more, preferably two, batteries 36. The batteries 36 may be twelve volt lead acid rechargeable vehicle batteries. The batteries 36, when disconnected from their charger, can be if desired the sole source of power for the system 10, powering both the heat exchange components within the housing 16 and the pump 33.

Figure 2:
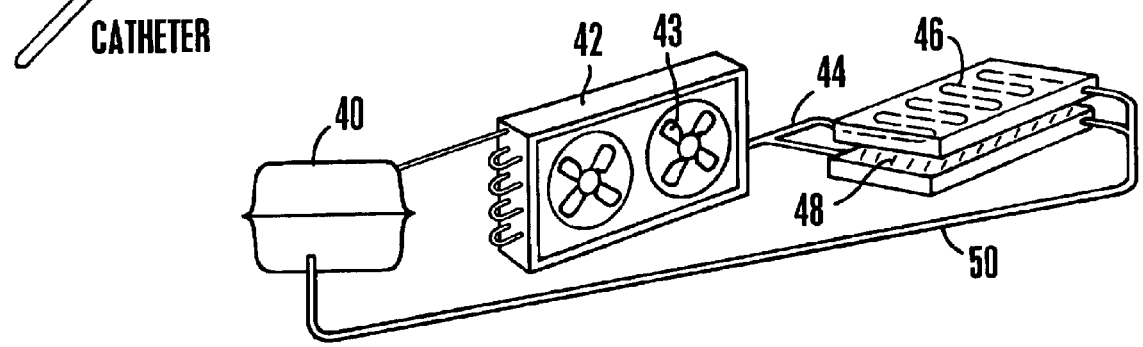
FIG. 2 is a perspective view of a compressor components of a first embodiment of the cooler.

FIG. 2 shows heat exchange components that can be included within the housing 16 in one non-limiting exemplary embodiment. As show, a Rankine cycle compressor 40 can compress refrigerant such as freon and send the freon to a condenser 42 with cooling fans 43, which receive air through the air intake 20 and exhaust air through the vents 22 (FIG. 1). The compressor 40 may be a Danfoss BD35F compressor. From the condenser 42 the freon flows through freon lines 44 to preferably two heat exchange plates 46 made of, e.g., copper or steel or other metal. A heat exchange element 48, mentioned above as being disposable in the slot 24 of the housing 16 and discussed further below, is sandwiched between the plates 46 in thermal contact therewith to cool the heat exchange element. After passing through the plates 46 freon is sent back to the compressor through return freon lines 50.

Figure 3:
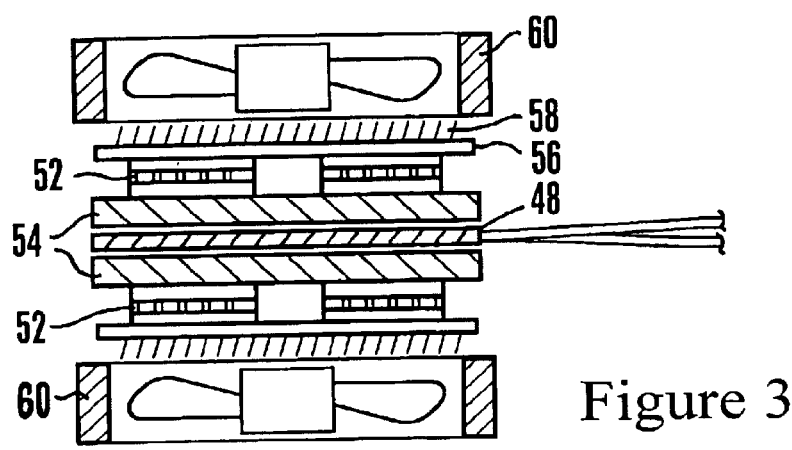
FIG. 3 is a perspective view of a thermoelectric cooler (TEC) components of a second embodiment of the cooler.

FIG. 3 shows that instead of a compressor-based system, the housing 16 of the system 10 can hold thermoelectric coolers (TEC) 52 that are thermally coupled with heat exchange cold plates 54 that sandwich the heat exchange element 48 and that consequently cool the element 48. Opposite the cold plates 54, the TEC 52 are thermally coupled to heat sink plates 56 in accordance with TEC principles known in the art, which may include cooling fins 58. Axial cooling fans 60 remove heat from the heat sink plates 56. The fans 60 can receive air through the air intake 20 and exhaust air through the vents 22 (FIG. 1).

Figure 4:
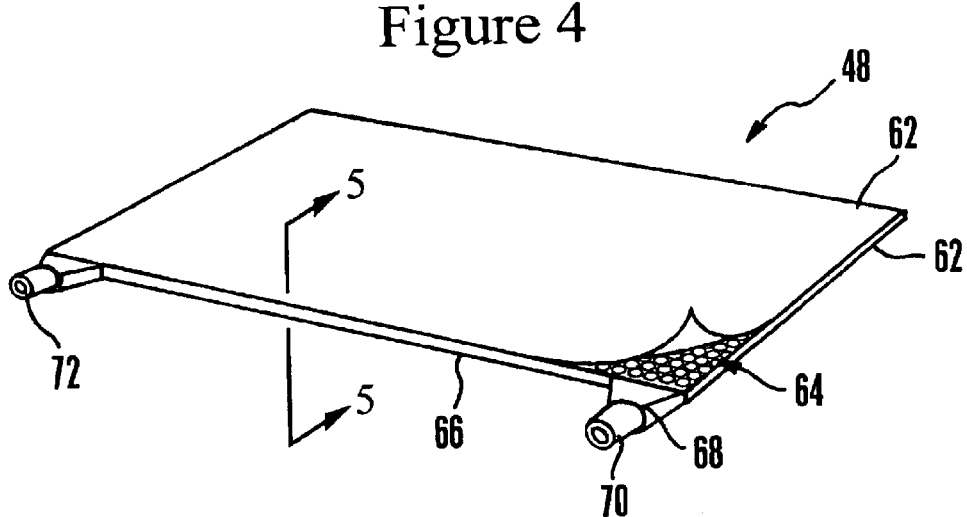
FIG. 4 is a perspective view of the disposable heat exchange element, with one of the edges turned up to expose the spacing spheres for illustration.
Figure 5:
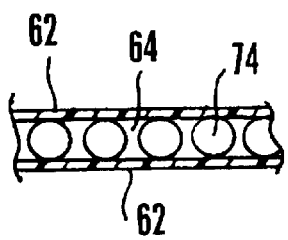
FIG. 5 is a cross-sectional view as seen along the line 5—5 in FIG. 4.

FIGS. 4 and 5 show a preferred non-limiting heat exchange element 48, which can be configured to have opposed flat flexible plastic layers 62 that form a coolant space 64 therebetween. A semi-rigid plastic receiving edge 66 may extend between the layers 62 and be formed with tubing receptacles 68 that receive respective segments 70, 72 of the inlet tubing set 26 and outlet tubing set 28 (segments 70, 72 also shown in FIG. 1). A tortuous path is established through which coolant can flow from the inlet receptacle 68 to the outlet. In a preferred non-limiting embodiment the tortuous paths are provided by hard plastic spheres 74, although other objects, such as egg-shaped objects, rectilinear objects and channels, and so on may be used.

Figure 6:
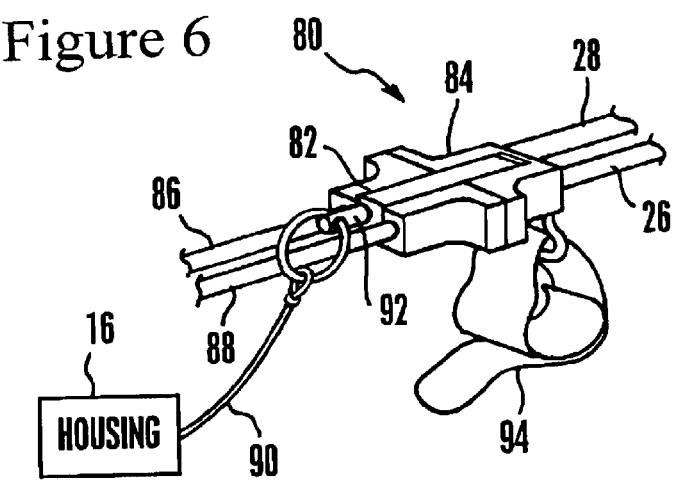
FIG. 6 is a perspective view of the quick disconnect connector in the engaged configuration, with portions broken away and schematically showing the housing 16.
Figure 7:
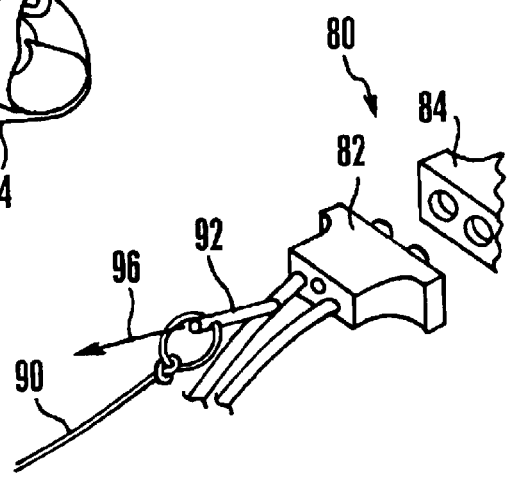
FIG. 7 is a perspective view of the quick disconnect connector in the disengaged configuration, with portions broken away.

The present recognizes that because the present system 10 is intended to be carried in an ambulance, the housing 16 may move suddenly, and that such movement could pose a risk of pulling the catheter 12, which is attached to the housing 16 by means of the tubing sets 26, 28, out of the patient. Accordingly, if desired a quick disconnect connector assembly, generally designated 80 in FIGS. 6 and 7, can be provided. The assembly 80 can have a first rigid half connector 82 that mates with a second rigid half connector 84 in fluid communication therewith, with the second rigid half connector 84 being connected to the inlet and outlet tubing sets 26, 28. In contrast, the first half connector 82 is connected to supply and return tubes 86, 88 that are in turn connected to the catheter 12.

A tether 90 may be connected to the first half connector 82 preferably by means of a pin 92, it being understood that the pin 92 engages and may hold together the half connectors 82, 84. The tether 90 is also connected to the housing 16, whereas the second half connector 84 preferably is attached, e.g., by means of a strap 94, to an object such as a gurney that is separate from the housing 16. With this structure, should the housing 16 move within the ambulance a sufficient amount, the tether 90 dislocates the pin 92 as indicated by the arrow 96 to decouple the half connectors 82, 84 (and, hence, the catheter 12 and housing 16) from each other, to prevent pulling the catheter 12 out of the patient. If desired one or both half connectors 82, 84 can be included with self-sealing valves that automatically close upon decoupling.

While the particular PORTABLE COOLER FOR HEAT EXCHANGE CATHETER as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for" or, in the case of a method claim, the element is recited as a "step" instead of an "act".

I claim:

1. A system for controlling patient temperature, comprising:
    a portable housing;
    a heat exchanger in the housing and powered by at least one battery;
    a heat exchanger element in thermal contact with the heat exchanger, the heat exchange element carrying coolant; and
    a closed loop heat exchange catheter outside the housing and receiving coolant from and sending coolant to the heat exchange element, the catheter being configured for placement in the circulatory system of a patient to exchange heat with the blood of the patient.

2. The system of claim 1, wherein the catheter is configured for percutaneous advancement into the central venous system of the patient.

3. The system of claim 1, wherein the coolant is not infused into the bloodstream of the patient.

4. The system of claim 1, further comprising a pump supported on the housing to pump coolant through the system.

5. The system of claim 1, further comprising:
    tubing connecting the catheter to the heat exchange element through a connector; and
    at least one quick disconnect assembly engaged with the housing and engaged with at least a portion of the tubing connected to the catheter to disconnect the catheter from the housing when the housing moves past a limit of the disconnect assembly.

6. The system of claim 5, wherein the disconnect assembly includes at least one tether.

7. The system of claim 1, wherein the heat exchanger includes at least one thermoelectric cooler (TEC).

8. The system of claim 1, wherein the heat exchanger includes at least one compressor.

9. The system of claim 1, wherein the heat exchange element forms an interior through which coolant flows and an exterior in thermal contact with the heat exchanger.

10. The system of claim 9, wherein coolant flows through the heat exchange element through tortuous paths.

11. The system of claim 10, wherein the tortuous paths are established at least in part by spheres disposed in the interior of the heat exchange element.

12. A method for cooling a patient while the patient is located in a vehicle, comprising:
    disposing a dc-powered heat exchanger in the vehicle;
    advancing a heat exchange catheter into the venous system of the patient;
    establishing fluid communication between the catheter and heat exchanger; and
    operating the heat exchanger to circulate coolant through the catheter to cool the patient.

13. The method of claim 12, wherein coolant does not enter the bloodstream of the patient.

14. The method of claim 12, wherein the catheter is advanced percutaneously into the patient.

15. The system of claim 1, wherein the battery is a lead acid battery.

16. The system of claim 1, wherein the battery is a twelve volt battery.

17. The system of claim 1, comprising two batteries.

18. The system of claim 1, wherein the battery is the sole source of power for the heat exchanger.

* * * * *